United States Patent [19]
Hooven et al.

[11] Patent Number: 5,433,721
[45] Date of Patent: Jul. 18, 1995

[54] ENDOSCOPIC INSTRUMENT HAVING A TORSIONALLY STIFF DRIVE SHAFT FOR APPLYING FASTENERS TO TISSUE

[75] Inventors: Michael D. Hooven, Cincinnati; Joseph C. Hueil, Loveland, both of Ohio

[73] Assignee: Ethicon, Inc., Somerville, N.J.

[21] Appl. No.: 91,807

[22] Filed: Jul. 15, 1993

Related U.S. Application Data

[63] Continuation-in-part of Ser. No. 937,324, Aug. 31, 1992, abandoned, which is a continuation-in-part of Ser. No. 822,478, Jan. 17, 1992, abandoned.

[51] Int. Cl.6 .............................................. A61B 17/00
[52] U.S. Cl. ................................... 606/143; 606/139; 606/142; 227/19; 227/175; 227/179; 227/180
[58] Field of Search ................... 606/1, 142, 143, 205, 606/207, 206; 227/175–179, 19; 604/95

[56] References Cited

U.S. PATENT DOCUMENTS

| | | | |
|---|---|---|---|
| 3,494,533 | 2/1970 | Green et al. | 227/175 |
| 4,060,089 | 11/1977 | Noiles | 606/151 |
| 4,445,509 | 5/1984 | Auth . | |
| 4,578,412 | 5/1986 | Kensey . | |
| 4,606,343 | 4/1986 | Conta et al. . | |
| 4,631,052 | 12/1986 | Kensey . | |
| 4,756,309 | 7/1988 | Sachse et al. . | |
| 4,781,186 | 11/1988 | Simpson et al. . | |
| 4,859,560 | 1/1990 | Papantonakos . | |
| 4,955,882 | 9/1990 | Hakky . | |
| 4,976,688 | 12/1990 | Rosenblum | 604/95 |
| 5,271,543 | 12/1993 | Grant et al. | 227/179 |

Primary Examiner—Stephen C. Pellegrino
Assistant Examiner—Jeffrey A. Schmidt
Attorney, Agent, or Firm—Paul A. Coletti; Robert L. Minier

[57] ABSTRACT

A drive mechanism for an endoscopic surgical instrument which has a rotatable drive shaft and a mechanism for translating the rotational force of the shaft for applying fasteners to tissue during endoscopic surgery.

17 Claims, 14 Drawing Sheets

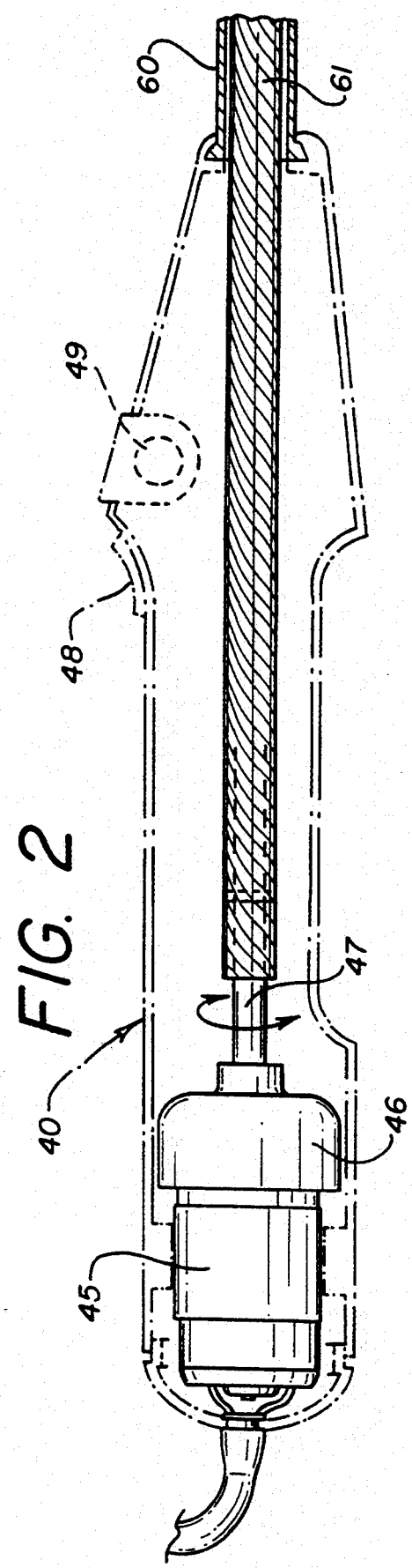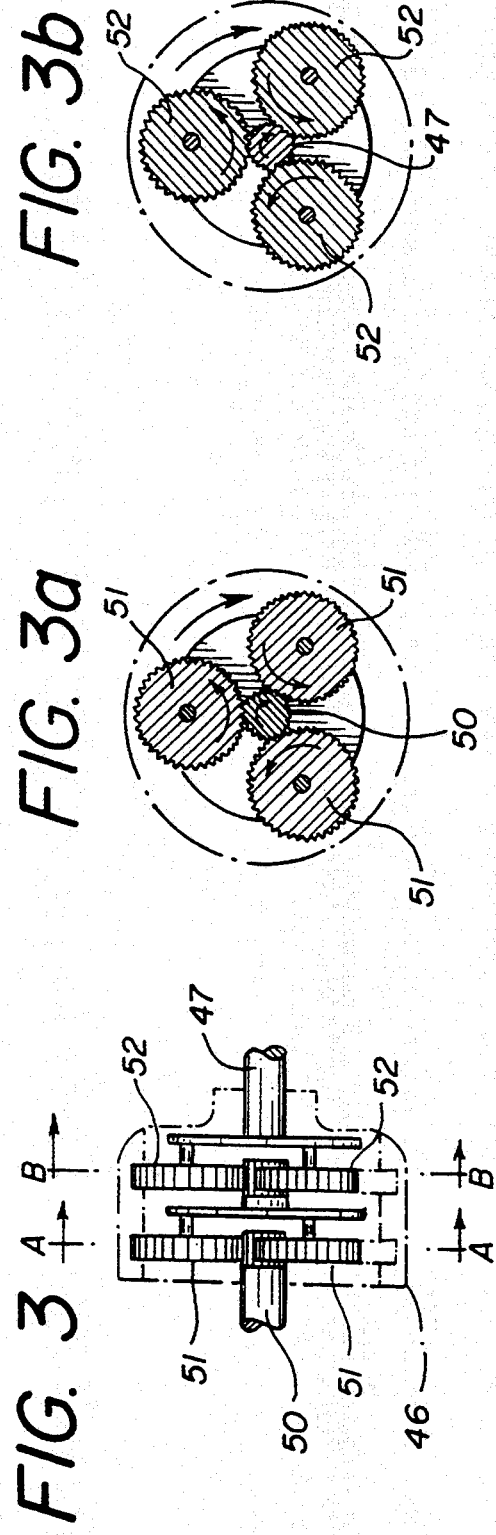

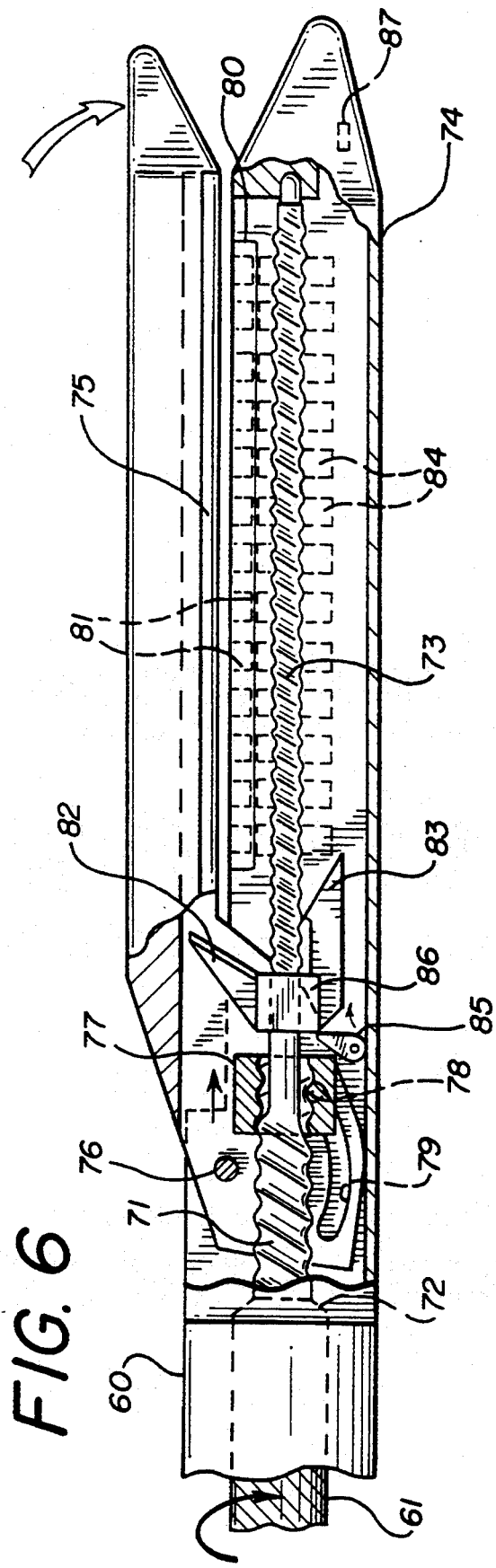
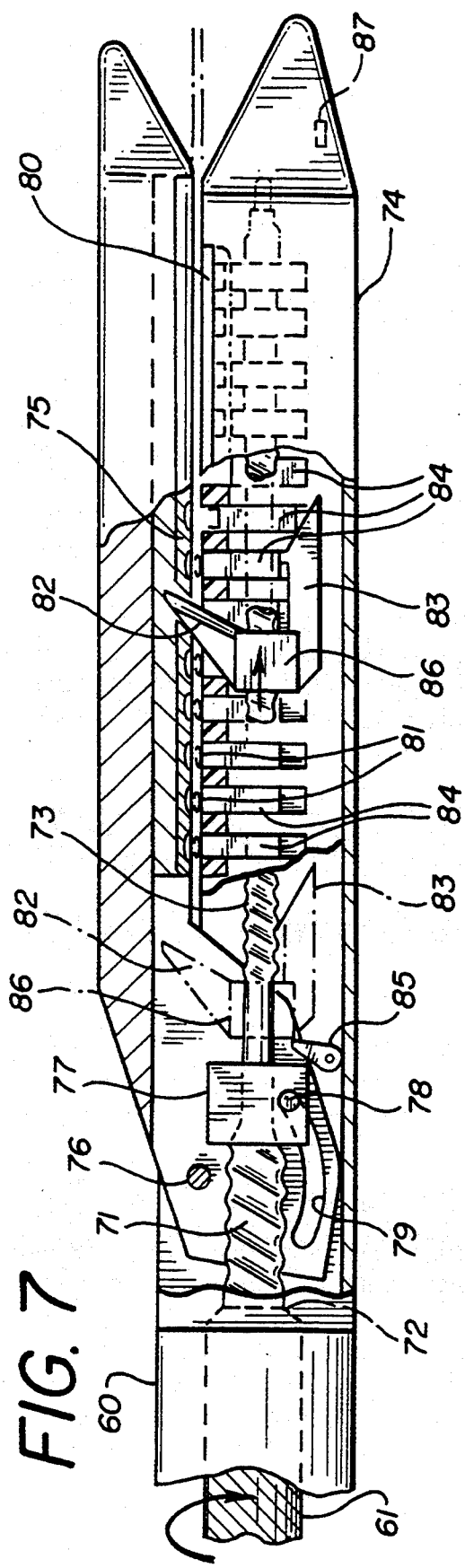

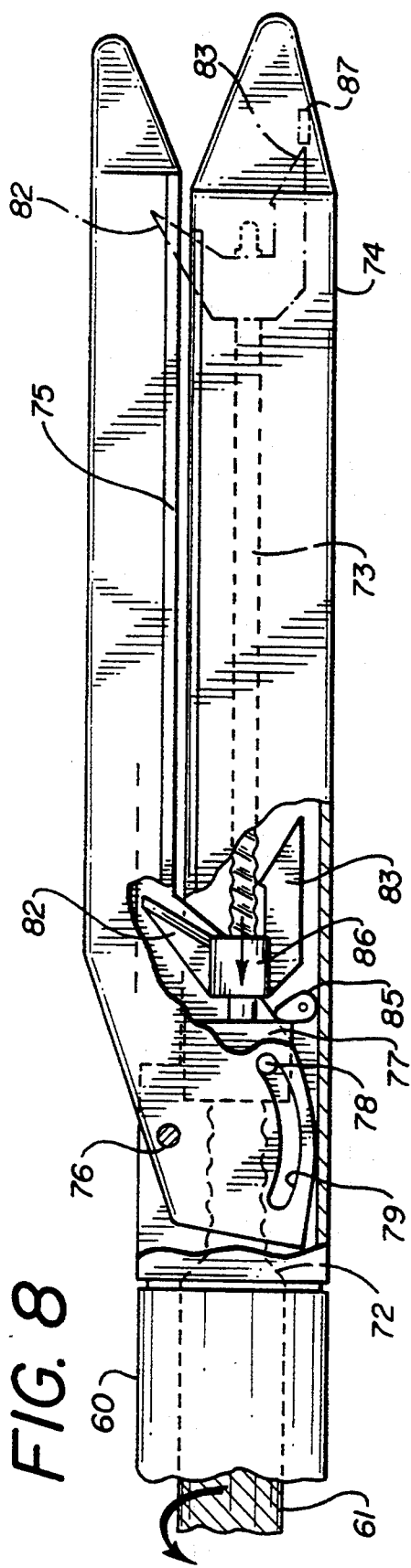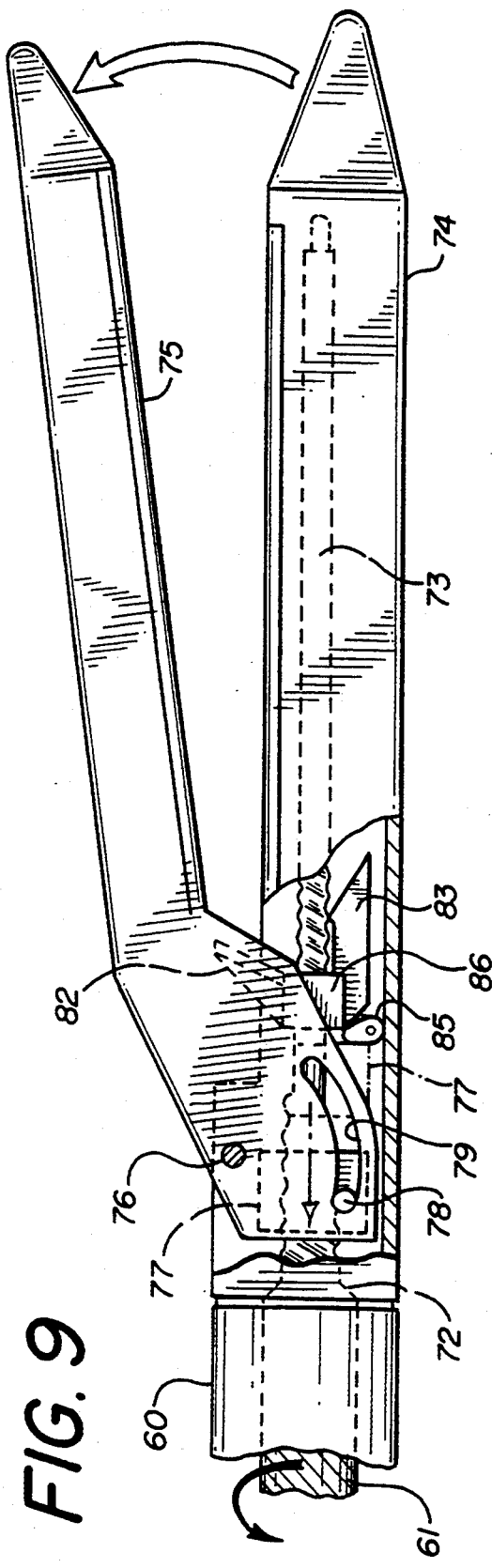

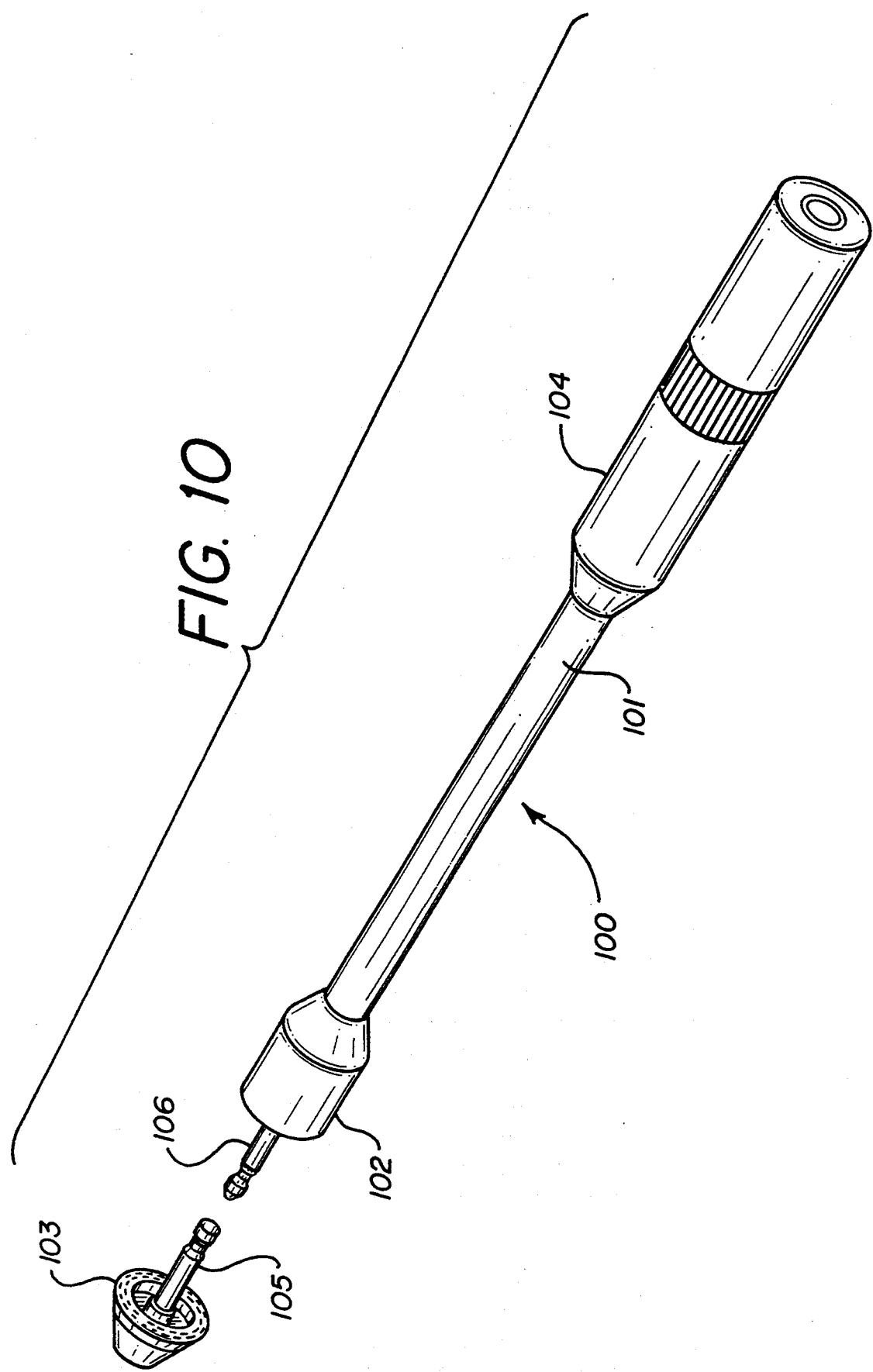

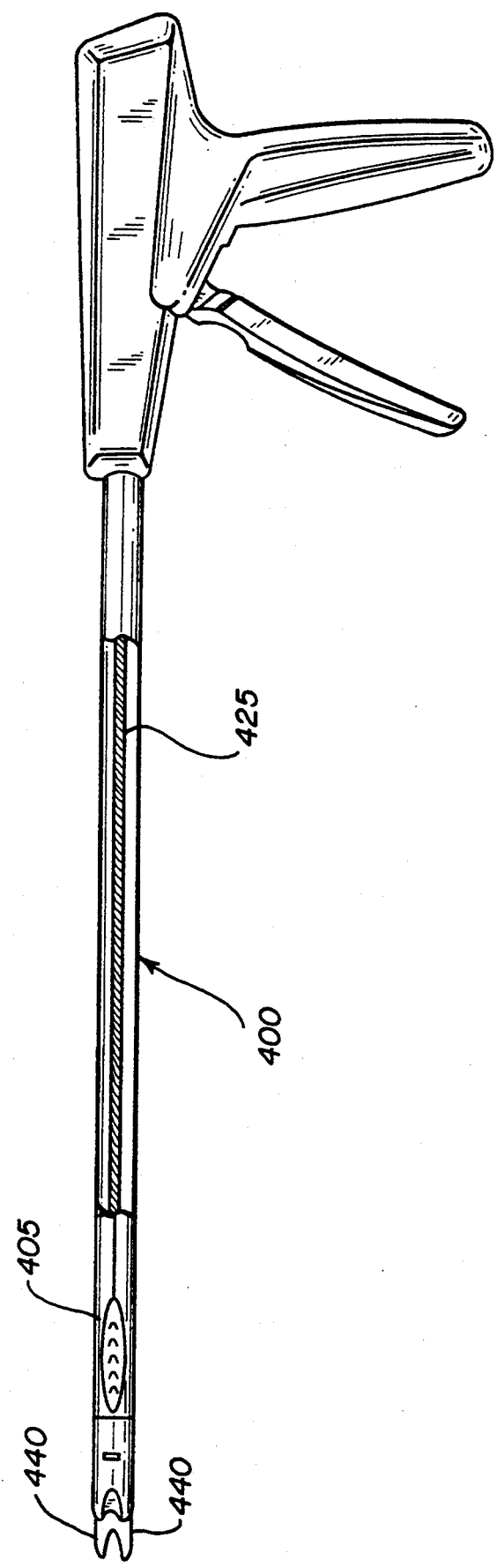

ENDOSCOPIC INSTRUMENT HAVING A TORSIONALLY STIFF DRIVE SHAFT FOR APPLYING FASTENERS TO TISSUE

RELATED APPLICATIONS

This is a continuation-in-part patent application of patent application Ser. No. 937,324 filed Aug. 31, 1992 now abandoned which is a continuation-in-part patent application of patent application Ser. No. 822,478 filed Jan. 17, 1992 now abandoned.

FIELD OF THE INVENTION

This invention relates to an improved drive mechanism for surgical instruments. More specifically, this invention relates to an improved drive mechanism for endoscopic instruments which reduces the amount of force which a surgeon must apply or use during a surgical procedure and in certain embodiments improves the access of the instrument within the surgical environment.

BACKGROUND OF THE INVENTION

Endoscopic surgery has been gaining wide acceptance as an improved and cost effective technique for conducting certain surgical procedures. In endoscopic surgery, a trocar which is a pointed piercing device, is sent into the body with a cannula placed around the trocar. After the trocar accomplishes piercing of the abdominal walls, it is removed and the cannula remains in the body. Through this cannula, endoscopic procedures are possible. Often, multiple openings are produced in the body with a trocar so that an endoscopic instrument may be placed in one cannula, appropriate viewing mechanisms placed in another cannula and fiber optics for illuminating the surgical field placed in yet another cannula. Generally, these endoscopic procedures take place under insufflation. As more is learned about endoscopic surgical procedures and more instruments developed, the type of procedures that may be performed endoscopically will increase. Presently, typical procedures are gall bladder removal, tissue repair, hernia repair and the like.

While endoscopic surgical procedures have substantial benefits to the patient, they do present certain problems to the surgeon conducting the procedure. For example, because the active part of the instrument is further removed from the manipulative part of the instrument, any slight movement of the manipulative part is magnified when it reaches the active part. Hence, when placing and forming a staple in tissue, the hand of the surgeon must be a lot steadier during the endoscopic procedure than if that same procedure was done during standard open surgery. The same can be said when severing vessels or incising tissue. Hence, in designing endoscopic surgical instruments, considerable effort is made to reduce the force required in order to operate or manipulate the instrument and allow the surgeon to have greater control over the instrument. Also, from an engineering standpoint, considerable design engineering is required to permit function of the active portion of the instrument given the physical limits of force and stroke of the surgeon's hand. Another problem in endoscopic procedures is that since the access to the surgical area is very limited, that is, through one or a few small incisions in the body, the access to the vessels, organs and tissue within the area in which the procedure is to be accomplished is very limited.

Most endoscopic instruments developed to date generate the larger forces required to drive staples through tissue and form the staples by using various mechanical levers, springs, or similar mechanical devices. Generally, a shaft extends from the handle of the instrument to the business end and linear forces are generated by this shaft through various mechanical means to drive staples through tissue or otherwise manipulate the business end of the instrument. In some instruments the shaft may be rotatable such as disclosed in U.S. Pat. Nos. 4,606,343 in order to move or position various parts of the business end with respect to each other. However, the forces required to drive staples through tissue and form the staples in the tissue are still generated by springs, levers, or other means which generate forces in a linear direction. In all instances, these forces are generated by the one manipulating the handle of the instrument and require considerable energy be exerted in order to apply the necessary forces.

Hence, it is desirable to produce endoscopic surgical instruments that can carry out a desired procedure; such as ligating vessels, stapling tissue, cutting tissue and the like, without physical restriction on the forces used to carry out these procedures and without such increased forces disrupting the operation and/or manipulation of the instrument. It is also desirable to produce endoscopic surgical instruments that allow for improved access to the surgical site; that is, the business end of the endoscopic surgical instrument may be moved about and positioned within the surgical site while still maintaining a single, small incision commonly used with such instruments.

SUMMARY OF THE PRESENT INVENTION

What I have discovered is an improved endoscopic surgical instrument. The instrument has a handle portion for manipulation outside the body and a business head for carrying out the desired procedure within the body; that is, stapling tissue, ligating vessels, cutting tissue and the like. The handle portion and the business head are connected by a housing. In the preferred embodiments of the present invention, the housing is flexible. Within the housing and extending from the handle to the business head is a rotatable drive shaft. In the preferred embodiments of the present invention the rotatable drive shaft is flexible. There are means disposed in the business head for translating the rotational forces, generated by the rotatable drive shaft into non-rotational forces, usually linear forces, for applying sufficient force at the business head of the instrument to cause fasteners to pass through tissue to be joined, to form the fasteners once passed through the tissue and/or cut the tissue.

In certain embodiments of the present invention, the instrument includes steering means for the business head which may be manipulated by mechanisms disposed in the handle portion. The steering means may manipulate both the flexible rotatable shaft and the business head to provide improved access within the surgical site.

DETAILED DESCRIPTION OF THE DRAWINGS

FIG. 2 is a longitudinal cross-sectional view of the handle of the endoscopic instrument depicted in FIG. 1.

FIG. 3 is detail of the gear reduction and assembly and handle.

FIG. 3a is a cross-sectional view taken along line a—a of FIG. 3.

FIG. 3b is a cross-sectional view taken along line b—b of FIG. 3.

FIG. 6 is an enlarged longitudinal cross-sectional view of the head of the instrument depicted in FIG. 5 with the head in a closed position.

FIG. 7 is an enlarged longitudinal cross-sectional view of the head of the instrument depicted in FIG. 5 with the head in a position of firing staples.

FIG. 8 is an enlarged longitudinal cross-sectional view of the head of the instrument of FIG. 5 with the head in the closed position after firing staples.

FIG. 9 is an enlarged cross-sectional view of the head of the instrument depicted in FIG. 5 with the head in the open position after the staples have been fired.

FIG. 10 is a perspective view of another embodiment of an endoscopic instrument in accordance with the present invention.

FIG. 10a is a view similar of yet another embodiment of an endoscopic instrument in accordance with the present invention, wherein the invention applies a series of ligating clips.

DETAILED DESCRIPTION OF THE INVENTION

Figure 1:
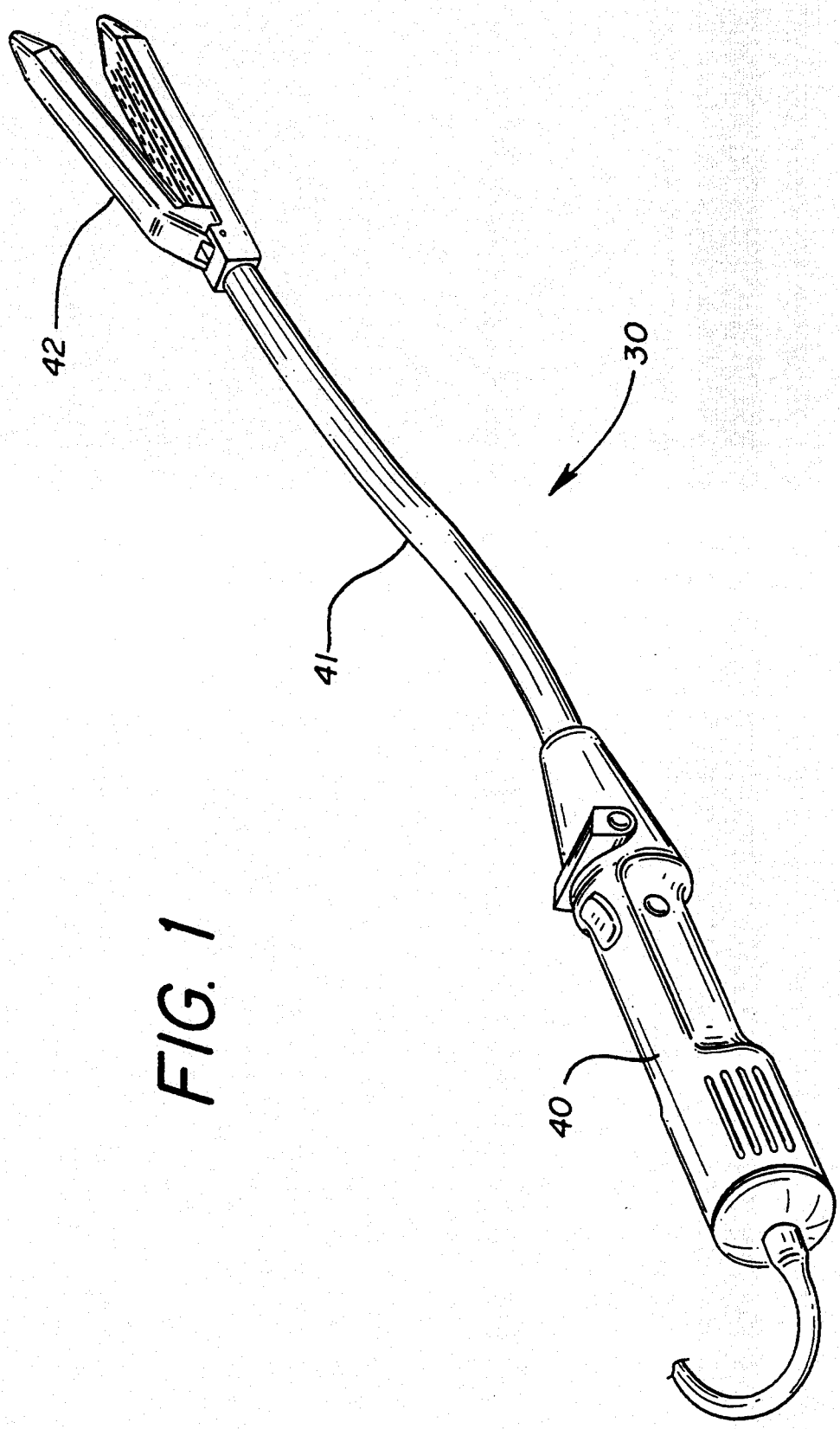
FIG. 1 is a perspective view of an endoscopic instrument in accordance with the present invention.

Referring to the drawings, there is shown in FIG. 1 a perspective view of an endoscopic instrument 30 of the present invention. The instrument has a handle portion 40. Extending from this handle portion is a housing 41 and at the end of the housing is a desired head or business portion 42 of the instrument. The head or business portion is that portion of the instrument which accomplishes a step in the surgical procedure, whether that be ligating, stapling, cutting, manipulating tissue or combinations of such steps. The head and housing of the instrument are constructed so that they can be applied through the cannula of a trocar as is well known in endoscopy.

In the embodiment depicted in FIGS. 1 through 9, the head portion is a linear stapler and cutter; that is, the head portion will place plural, parallel rows of staples with the staples offset in adjacent rows. The instrument will also operate a knife to pass between two adjacent rows of staples. Such an instrument is used to staple tissue together and cut the tissue between the stapled portions. Such instruments are used in various types of surgical procedures such as bowel and lung resections.

FIG. 2 is an enlarged longitudinal cross-sectional view of the handle portion of the instrument depicted in FIG. 1. In this embodiment, the handle portion includes a small DC motor 45 attached to a gear box 46. Extending from the gear box is a rotatable, flexible, drive shaft. The rotatable, flexible, drive shaft extends substantially the length of the handle. Also included in the handle and interconnected with the DC motor are a suitable on-off switch 48 and a switch 49 to control the power being supplied by the motor. While in this embodiment the motor itself is included in the handle, it should be appreciated that the motor could be separate from the instrument with appropriate connections so that a variety of instruments can be used with a detachable motor or power source.

As depicted in the cross-sectional views in FIGS. 3, 3a and 3b, the motor shaft 50 extends into the center of the gear box 46. The gear box comprises two sets of gears 51 and 52 which reduce the rotation of the shaft 47 with respect to the motor at a ratio of 36:1 or other reductions as desired.

Figure 4:
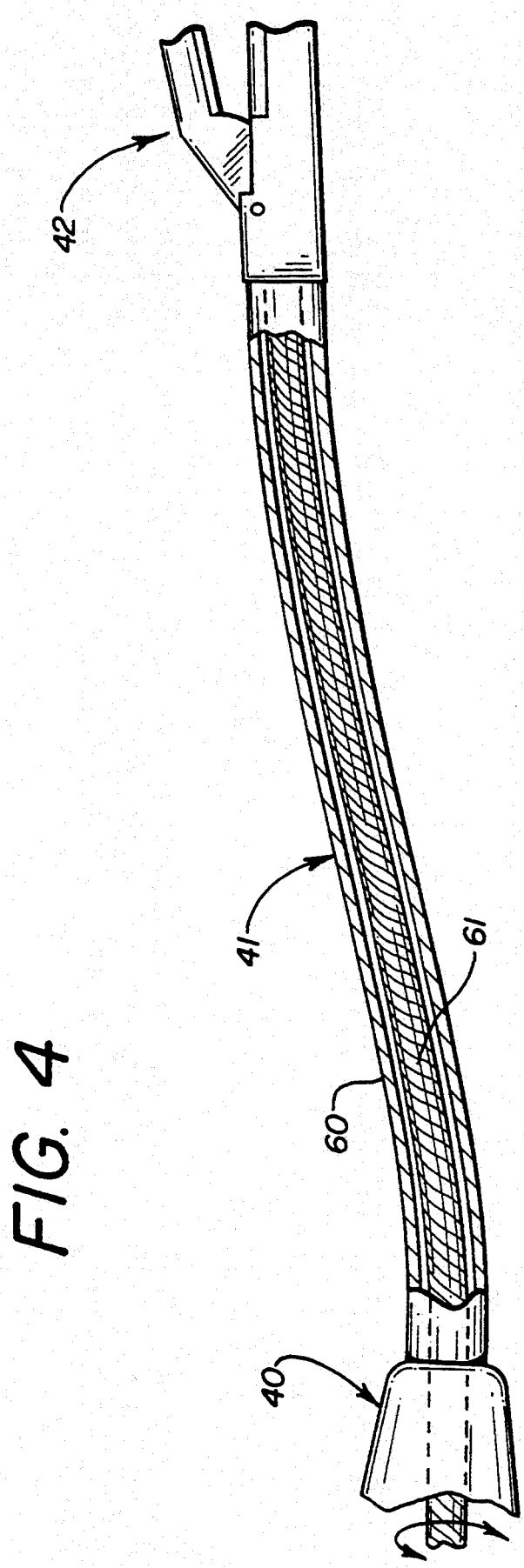
FIG. 4 is a longitudinal cross-sectional view of the shaft of the system depicted in FIG. 1.
Figure 5:
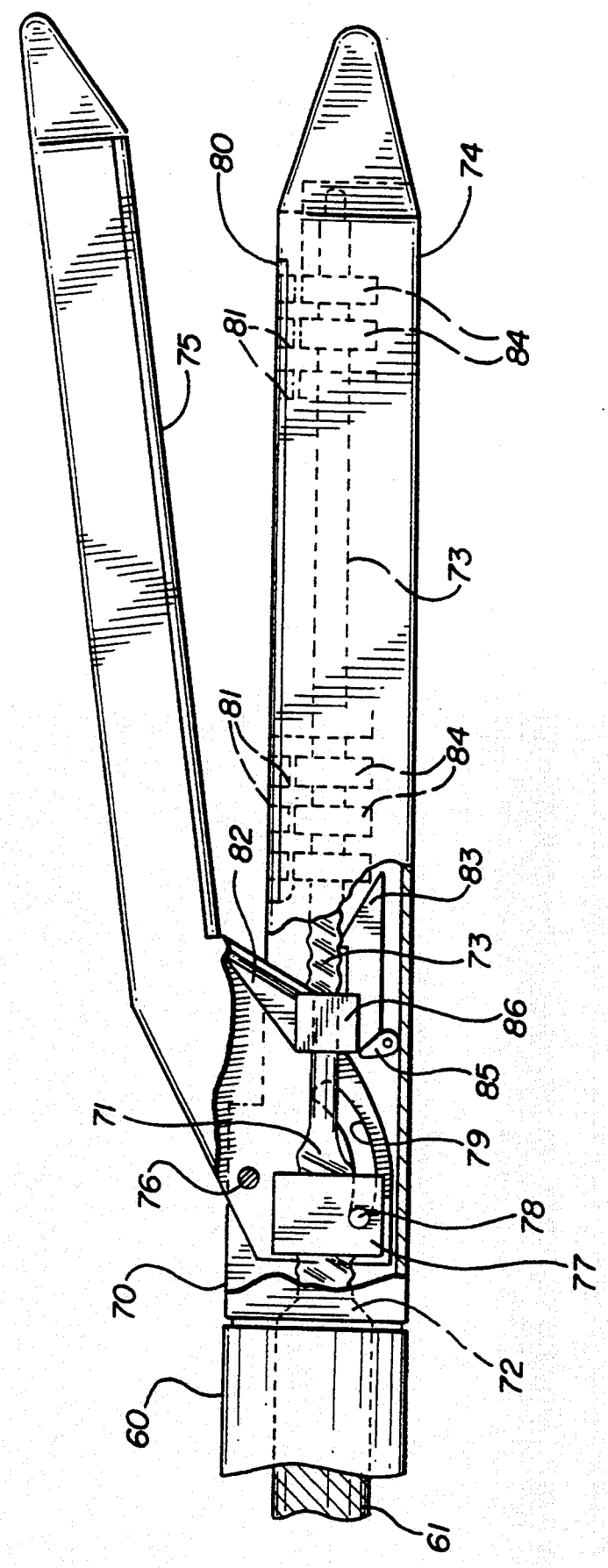
FIG. 5 is an enlarged longitudinal cross-sectional view of the business head of the instrument depicted in FIG. 1.

Referring to FIG. 4, there is shown an enlarged longitudinal cross-sectional view of the housing of the instrument shown in FIG. 1. In this embodiment, the housing 60 is flexible. Through the center of the housing, there extends a rotating, axially flexible, torsionally stiff, drive shaft 61. The housing connects the handle of the instrument to the head of the instrument and the flexible drive shaft is connected to the shaft 47 as shown in FIG. 2.

FIGS. 5 through 9 are enlarged cross-sectional views of the head portion of the instrument depicted in FIG. 1. The views depict the head of the instrument in the open position prior to being placed on tissue (FIG. 5), in the closed position ready for firing (FIG. 6), during the firing action (FIG. 7), after the firing action has been completed (FIG. 8) and in the final open position (FIG. 9) when the instrument may be removed. In these figures, like parts are identified with the same numerals. The housing 70 of the head is suitably connected to the shaft housing 60 either by a press fit or ultrasonic welding or other similar means. Extending substantially the length of the head and connected to the rotating drive shaft 61 is a threaded rod 71. The threaded rod has a larger diameter portion 72 adjacent the drive shaft 61 and a smaller diameter portion 73 for the remainder of the threaded rod. The head includes a staple or staple cartridge portion 74 and an anvil portion 75. The staple portion and the anvil portion are pivotally connected to each other by the anvil pivot pin 76. Mounted on the larger diameter portion of the threaded rod is a closure nut and extending from that closure nut 77 is a closure pin 78 which moves in slot 79 disposed in the pivotally anvil portion of the head. When the flexible drive shaft rotates, the threaded rod also rotates and on rotating the closure nut moves down the threaded rod and moves the closure pin in the closure slot to close the anvil portion against the staple portion of the instrument. Tissue to be treated or manipulated is placed between the anvil portion and the staple portion of the head of the instrument while the head is in the open position. Power is applied to the flexible drive shaft to rotate the drive shaft and the threaded rod and close the anvil portion.

Mounted in the staple holding portion of the instrument is a removable staple cartridge 80. The cartridge holds four rows of staples 81. The rows are parallel and in adjacent rows the staples are off-set as is well known in the art. The cartridge is placed so that it is opposite the anvil portion of the instrument and snaps into the staple holding portion of the instrument as shown. As depicted in the Figures, extending the length of the staple portion of the instrument, is a smaller diameter portion of the threaded rod. Mounted on this rod to move along the rod as the rod rotates is a knife member 82 and a driving wedge member 83 which are interconnected. The wedge member precedes the knife member as they move along the threaded rod. As the wedge member moves down the threaded rod, it drives the staples out of the cartridge via the individual staple drive members 84. The staples pass through the tissue and against the anvil to form the staples in the tissue. The knife 82 following the driving wedge cuts the tissue between adjacent rows of staples. The driving wedge is actually two pieces; that is, it has one wedge piece on one side of the knife to drive the staples on that side of the knife and a similar wedge piece on the opposite side of the knife to drive the staples on that side of the knife. When the anvil portion 75 is closed as shown in FIG. 6, the closure nut 77 moves a stop member 85 forward so that the firing member 86 on which the knife 82 and wedges 83 are disposed is moved forward and engages the threads of the smaller diameter portion 73 of the threaded rod to move forward along the rod and drive the staples 81 and cut tissue. The firing member 86 is biased using a suitable means so as not to engage the threaded rod until the stop member is activated. Once the firing member has moved to its most forward position to drive and form all of the staples and cut tissue, it engages a suitable contact 87 which immediately reverses the motor to retract the firing member. In its fully retracted position, the firing member 86 moves the stop member 85 rearwardly causing the closure nut 77 to retract and open the anvil portion 75 of the head of the instrument.

As shown in FIGS. 10 through 13 there is shown an endoscopic intraluminal stapling instrument. As shown in FIG. 10, the intraluminal stapling instrument 100, comprises a centrally disposed longitudinally extending endoscopic section 105. Disposed at one end of the section is the business end 102 of the instrument which carries a circular array of tissue fasteners. Removably attachable to this business end is the anvil portion 103 of the instrument which is used to secure the fasteners after they have been placed through tissue to be joined. At the opposite end of the endoscopic section is the handle 104 of the instrument. The handle may be attached to a suitable power means (not shown) as will hereinafter be explained. In use, the business end of the instrument may be passed completely through one end of the vessel to be joined. The other end of the vessel to be joined is slipped over the anvil. The section of the vessel slipped over the anvil is tied about the circular shaft 105 with a purse string suture as is well known in the art. The opposite end of the vessel to be joined is also tied with a purse string suture about the fastener head shaft 106. The anvil is then attached to the head of the instrument and the instrument fired to form a circular array of staples joining the two vessel ends. A knife, disposed in the head of the instrument may then be actuated to cut away excess tissue inside the lumen of the joined vessel.

Figure 11:
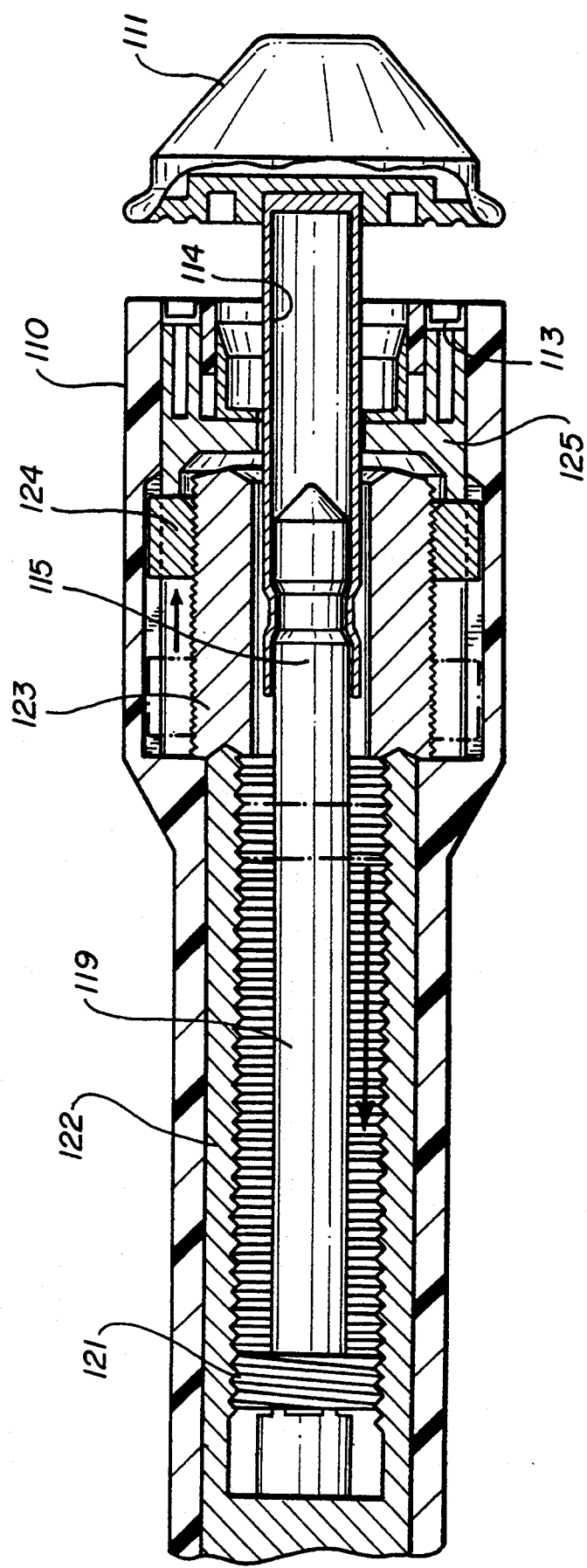
FIG. 11 is an enlarged longitudinal cross-sectional view of the business head of the instrument depicted in FIG. 10 with the head in an open position.
Figure 12:
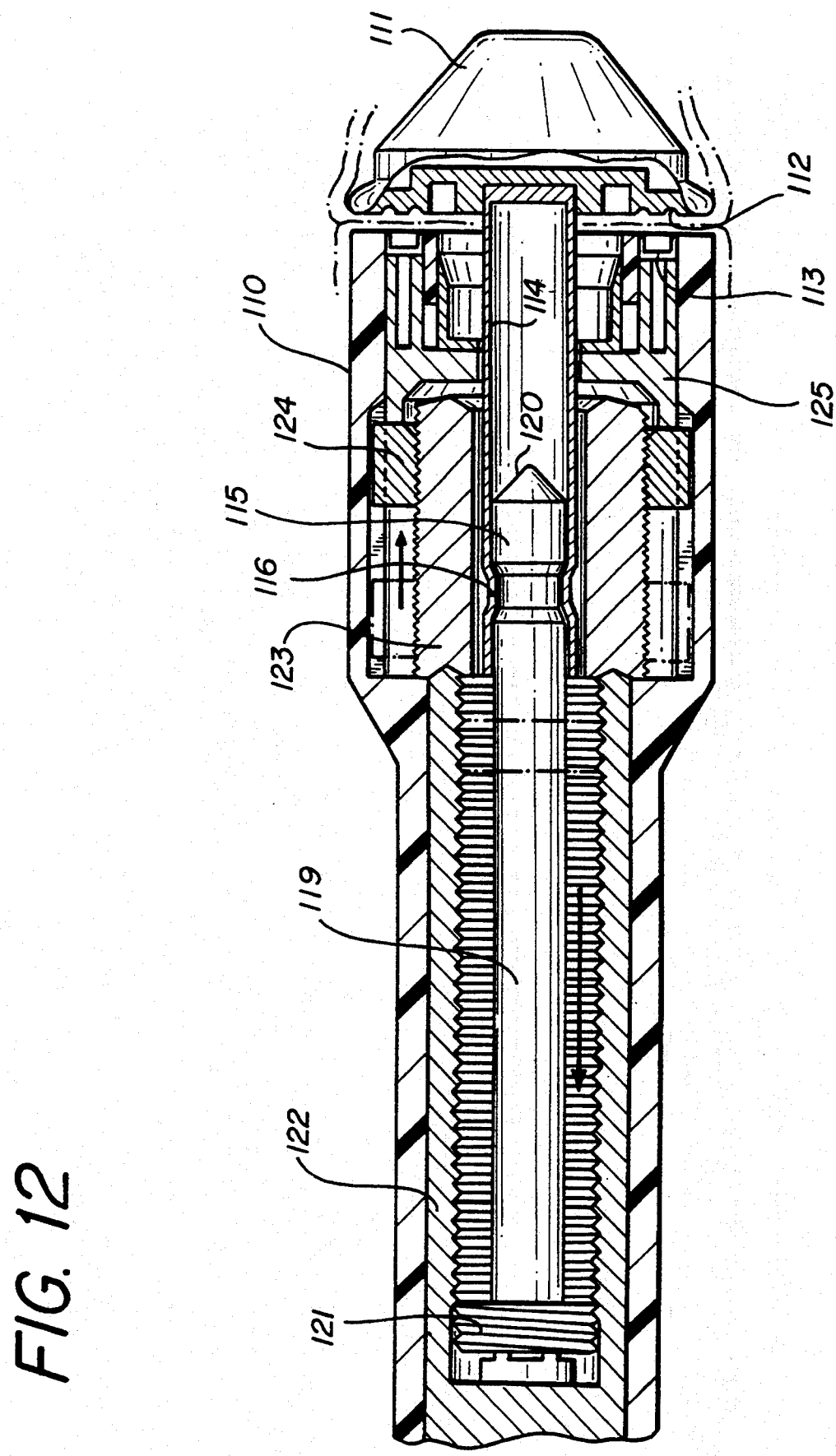
FIG. 12 is an enlarged longitudinal cross-sectional view of the head of the instrument depicted in FIG. 10 with the head in a closed position.
Figure 13:
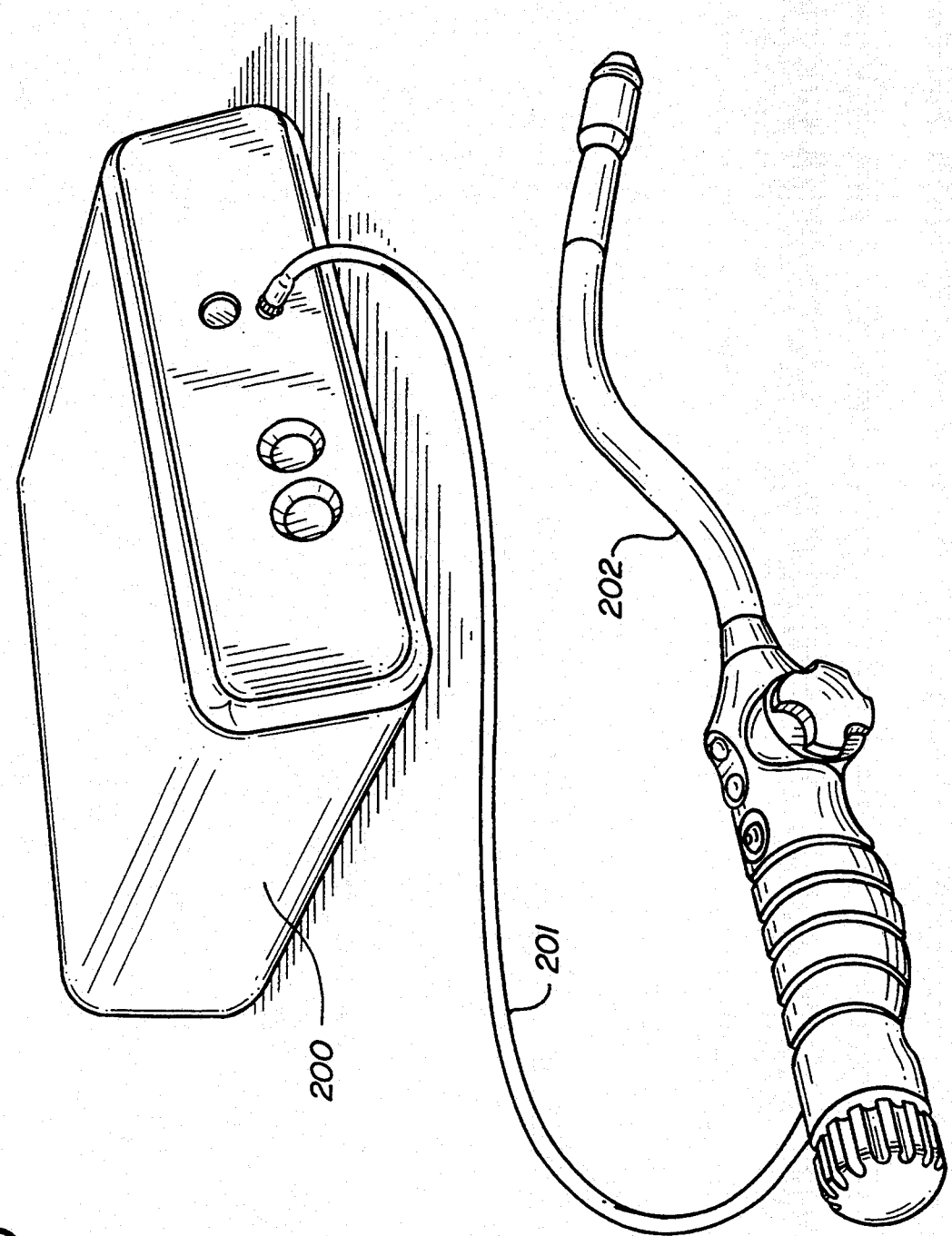
FIG. 13 is a perspective view of a system incorporating an instrument of the present invention.
Figure 14:
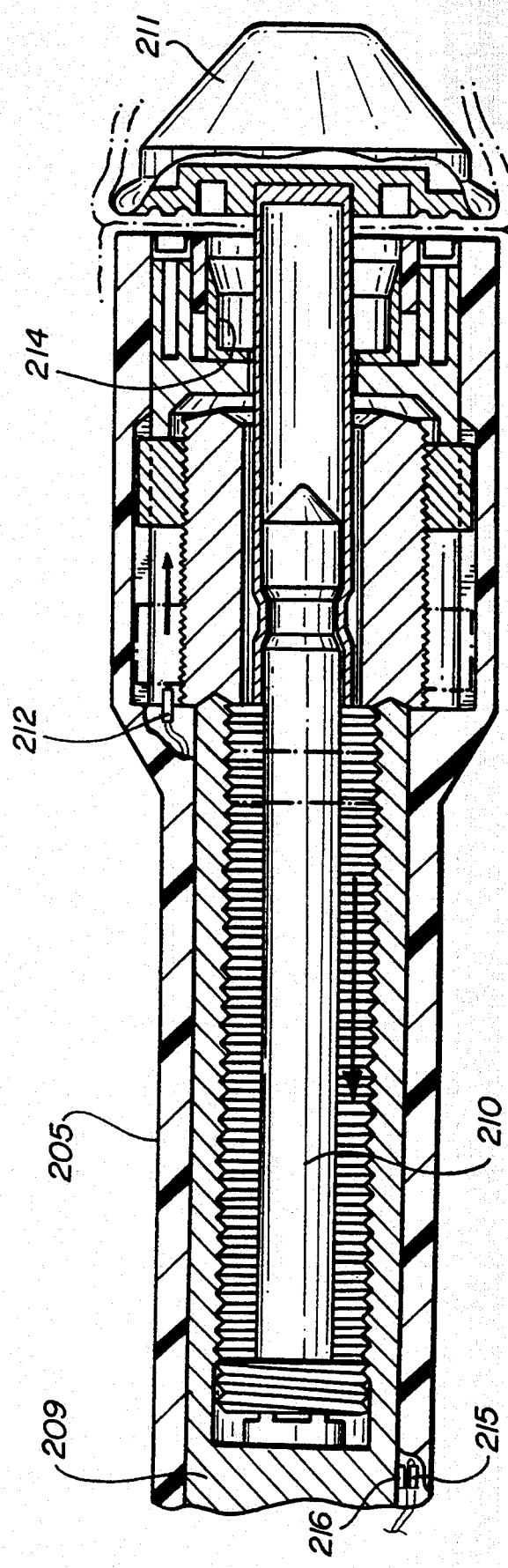
FIG. 14 is a cross-sectional view of the head of the endoscopic instrument depicted in FIG. 13.
Figure 15:
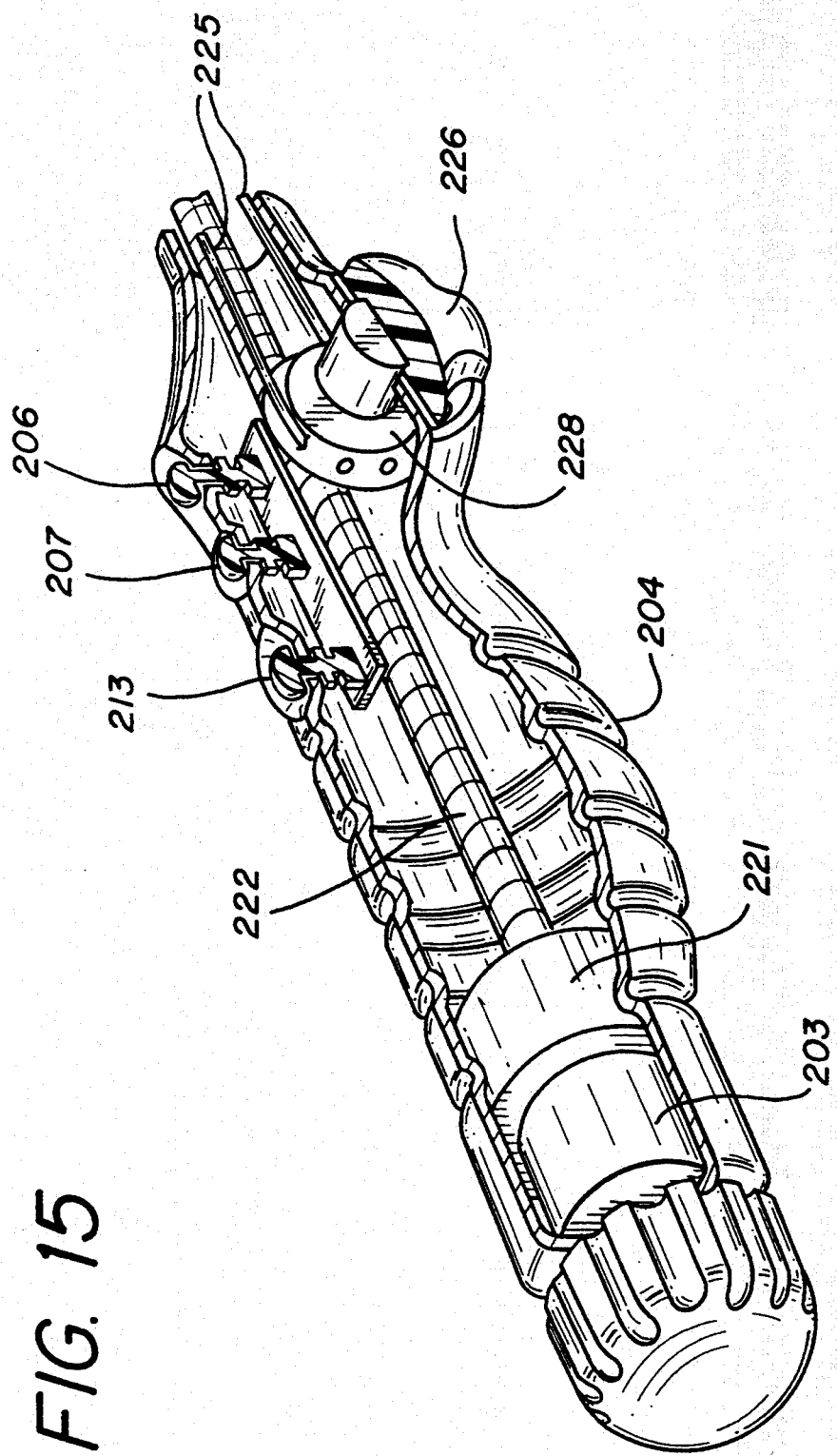
FIG. 15 is a partial cut-away perspective view of the handle portion of the instrument depicted in FIG. 13.
Figure 16:
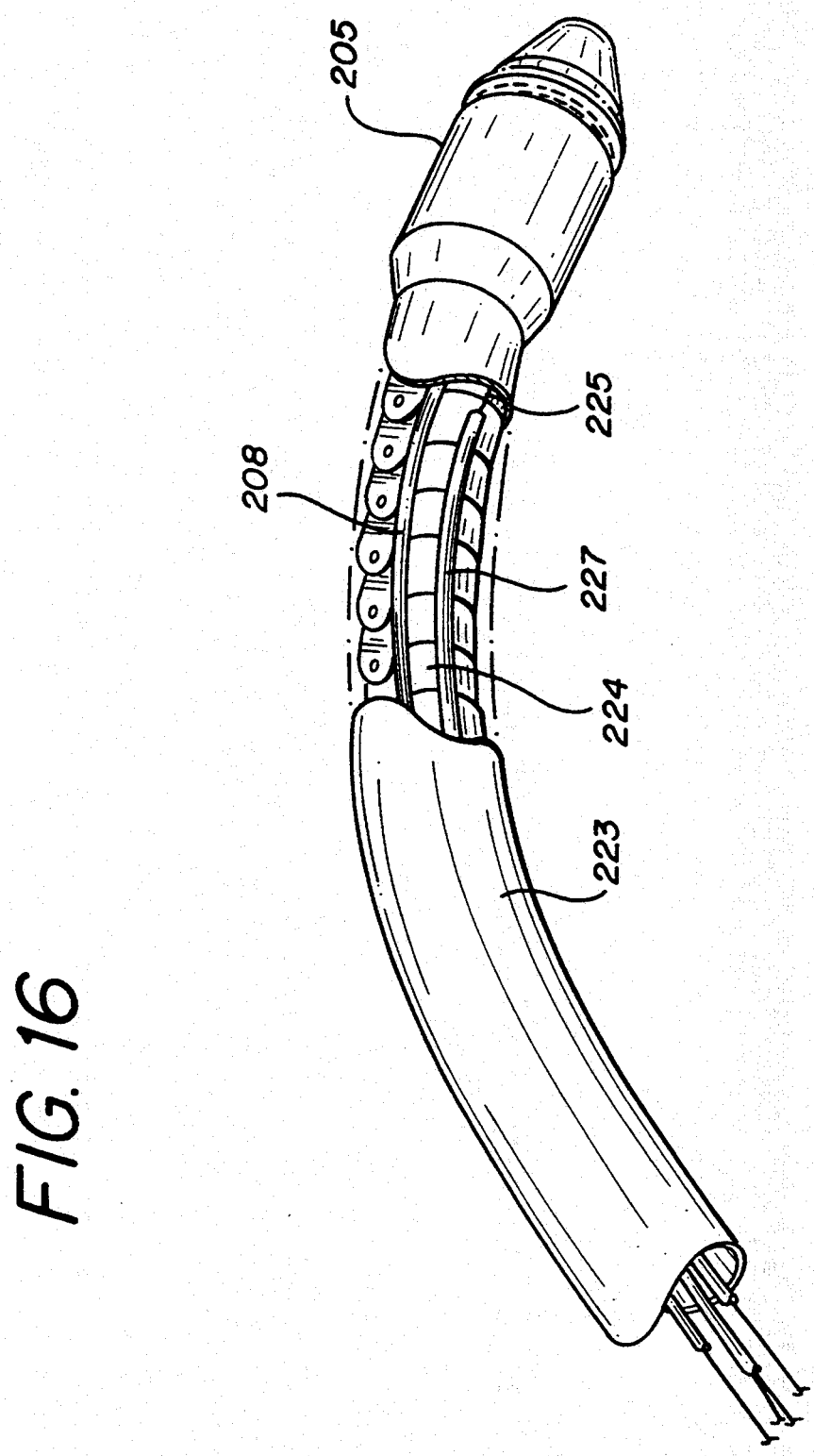
FIG. 16 is a partial cut-away perspective view of the flexible shaft portion of the instrument depicted in FIG. 13.

As is more clearly shown in FIGS. 11 and 12, the business end or head of the instrument comprises a staple or fastener carrying portion 110 and a detachable anvil 111. FIG. 11 shows the anvil detached from the head of the instrument and FIG. 12 shows the anvil attached to the head of the instrument. On the anvil head there are contained a plurality of depressions 112 displayed circumferentially around the anvil head. These depressions correspond to the staples 113 or fasteners held circumferentially within the head. The anvil may be placed within the lumen of tissue to be joined and the tissue tied down about the shaft 114 of the anvil using a purse string suture. The shaft of the anvil is then pressed on to the trocar 115 so that the indentation 116 in the anvil fits the indentation of the trocar. There is a suitable alignment mechanism on the trocar and the anvil shaft to insure that the staples in the business head will align with the depressions in the anvil head. The business head of the instrument includes a centrally located trocar 115 which is longitudinally movable along the longitudinal axis of the business head. The trocar is a solid shaft 119 which has a pointed piercing end 120 at one end thereof. The opposite end of the trocar shaft carries a threaded member 121 attached to the trocar shaft. The threaded member rides in a hollow tube 122 having its inside surface appropriately threaded so that the member rides along the threaded surface. The inside threaded hollow tube is keyed to the rotatable shaft that extends down the endoscopic section of the instrument so that both rotate together. As they rotate in one direction, the threaded member on the trocar shaft will move forwardly extending the trocar to its most forwardly extended position as seen in FIG. 11. When they rotate in the opposite direction, the trocar shaft will be retracted to a closed position as seen in FIG. 12. Attached to the end of the hollow inside threaded tube opposite the end keyed to the rotatable shaft is a second threaded hollow tube 123. However, this tube is threaded on its outside surface and is threaded in the opposite direction to the threads on the inside of the hollow tube 122. Furthermore, the pitch of the threads on the outside of this hollow section are less than the pitch of the threads on the inside of the hollow tube. A threaded nut 124 fits over this outside threaded tube. The business end of the instrument carries a circular array of staples. Disposed inwardly of this circular array of staples is a circular knife. A staple and knife driver 125 is positioned in the head to drive the staples and knife. When the rotatable shaft is rotated so as to retract the trocar and bring the anvil head down on to the business end of the instrument, the threaded nut on the outside threaded hollow section moves forwardly until it engages the driver. As the rotatable shaft continues to rotate, the threaded nut drives the staples through the tissue placed between the anvil and business end to join the tissue. Thereafter it also drives the knife through the tissue to cut inwardly extending tissue that is purse stringed down around the anvil shaft. The rotatable shaft is then reversed which allows the threaded nut to move back towards the handle of the instrument and the trocar to move forwardly, open the anvil and open the instrument so that it may be removed from the now fastened lumina.

The handle of the instrument depicted in FIGS. 11 and 12 is similar to the handle described and depicted with regard to FIG. 2. One end of the handle attaches to the endoscopic section. The rotatable shaft which extends down the endoscopic section extends into the handle and is attached to a set of planetary gears. The opposite side of the planetary gear train is attached to a shaft having a hexagonal slot or key that an appropriate power source may be inserted into the hexagonal slot to drive the planetary gear train. The planetary gear used provides a gear reduction of approximately 90:1 for the rotatable shaft.

Rotatable flexible shafts are available from a number of manufacturers such as the Stow Manufacturing Company, the Suhner Manufacturing Corporation, and SS White Industrial Products Corporation. The shaft will be 8 to 10 inches long and should be as small a diameter as suitable for whatever operation is to be carried out. The casing for the shaft must be constructed so that the free end of the shaft will resist whatever torque is being applied in the operation of the instrument. The magnitude of the torque will, of course, vary as to the type of operation of the instrument (i.e., stapling, cutting, etc.) but the deflection of the casing should be kept to a minimum. The connection of the shaft to the drive should be as simple as possible. An embodiment similar of the embodiment described in FIG. 5-9 is shown in FIG. 10a. Therein, the endoscopic mechanism comprises an endoscopic clip applier 400 which is capable of applying clips 405 using a pair of jaws 440 squeezed into position, such as those seen in FIG. 10a. The drive shaft 425 is similar to that of the drive shaft 61 of FIG. 5. Accordingly, operation of this mechanism is similar to that of FIGS. 5-9 and 10. It will be readily understood by those skilled in the art that the principles applicable for applying staples as in FIG. 10 are similarly applicable for applying ligating clips 405 as in FIG. 10a.

A steerable embodiment of the endoscopic instrument of the present invention is depicted in FIGS. 13 through 16. The system depicted consists of a microprocessor 200, a tether 201 connecting the microprocessor to an electromechanical circular stapler 202 of the present invention.

The microprocessor serves as a power supply for the electronics of the system as well as the supply for the DC voltage and current necessary to cause rotation of the motor 203 housed in the handle 204 of the stapler.

The microprocessor contains the componetry necessary to supply the proper voltage and current as well as the circuity necessary to control the logical sequence of steps of a complete cycle of the stapler. The logical sequence is controlled along with the other switches and sensors and components of the system.

The head 205 of the stapler contains electronic sensors which detect motion of the staple forming and tissue cutting components located within the head. The electrical switches 206 and 207 on the handle of the stapler control the flow of electric power between the microprocessor, motor, and sensors in the head of the stapler. Electrical conductors running in sheaths 208 along the neck of the shaft of the stapler, within the handle of the stapler and the tether connecting the microprocessor to the stapler, conduct the electric current used throughout the system.

When switch 206 is depressed, it allows current to flow to the motor and causes its main shaft to turn in a counter-clockwise direction. This rotation is passed through the drive train to the power nut 209 in the head and to the mating thread on the bottom of the trocar 210. This motion increases the staple forming gap by raising the anvil and/or extends the point of the trocar past the top plane of the head of the stapler. The anvil 211 and anvil shaft can be removed as an assembly from the trocar when the staple forming gap is relatively large.

When switch 207 is depressed, it allows current to flow through the motor and turn the output shaft in a clockwise direction. This direction of rotation has the opposite effect so the staple forming gap will decrease in size as the anvil approaches the top plane of the stapler head and the trocar will retract within the head of the stapler.

This closing motion is stopped by a limit switch 212 within the head when a predetermined and controllable staple forming gap is reached between the top plane of the head of the stapler and the bottom side of the anvil.

Until such time that the limit switch contacts are switched, and before the predetermined staple forming gap is reached, the fire switch 213 on the handle is electrically inoperative. The instrument will not form staples or move the knife forward while the staple forming gap is above a predetermined distance.

Once the proper and predetermined staple forming gap has been reached, the fire switch 213 is made operable by the same limit switch 212 and associated circuitry. Once operable pressing the fire switch will cause current to flow to the motor so that its rotation causes the staple drivers and circular cutting knife to advance toward the anvil on the mating 0.025 in. pitch threads, pushing the staple through the tissue and clinching the tissue while cutting it with the circular knife 214.

Inductive sensor 215 will sense the number of times the magnetic media 216, attached to the power nut, passes in close proximity to it, and sends electrical signals down the neck of the instrument, through the tether and on to the microprocessor. The microprocessor will convert these signals into equivalent revolutions of the power nut which is synchronized to the pitch of the threads and hence, the distance the drivers and knife must advance to complete the form and cut steps of the cycle.

After the required number of revolutions of the power nut is counted by the microprocessor, it will stop the motor rotation and restart it in the opposite direction so that the knife is retracted back into the head and the staple forming gap is increased in an amount such that the stapled and cut tissue can easily be removed from the stapler.

The motor 203 is a DC permanent magnet motor whose output shaft is connected to a planetary gear train within the gearhead 221. The combination of gear diameters within the gearhead, through which the rotation must be transmitted, slows the rotational speed in an approximate 1:90 ratio. As the speed of rotation is decreased, the torque (turning force) at the output shaft of the gearhead is increased roughly in the same inverse 90:1 ratio. This torque is then passed through the drive shaft and into the stapler head which contains the mechanical components which form the staples and cut the tissue via threads and rotary motion. The combination of rotational speed reduction and thread pitch sets the speed at which the trocar will open and close as well as the speed at which the staple and tissue cut functions are completed. The rotational speed is selected and set so that the instrument operates at a speed that the operator finds convenient.

The drive shaft 222 is a braided wire cylindrically shaped component that has ends configured so that one end is easily attached to the output shaft of the gearhead and the other end to the power nut 207 within the head of the stapler near the base of the stapler head. The drive shaft is of braided construction so that it is transversely flexible while torsionally much more rigid. These qualities allow the shaft to bend easily along its length while being rigid enough to transmit the torque necessary to cause the components within the head to turn and thus to form the staples and cut the tissue.

The above described flexible drive shaft is housed within a similarly flexible outer housing 223. This outer housing protects the patient from contact with the rotating drive shaft and also resists the torque of the drive shaft so the necessary torque can be applied to the components within the head. If the flexible drive shaft housing were not torsionally rigid, the transmitted torque would twist the outer housing and tend to rotate the head of the stapler the same amount as the housing twists which is undesirable.

The flexible drive shaft housing ends each have a coupling means which allows easy but firm attachment to the handle of the stapler and to the base of the stapler head.

The flexible drive shaft housing can be constructed using special pivoted steering knuckles 224 which can aid in the positioning of the flexible shaft and stapler head to the sight where the stapling will be done. The steering system consists of a flexible drive shaft outer housing with the pivoted steering knuckles all along its length or at desirable intervals along its length. Steering wires 225 run from the handle to attachment points on the steering knuckles. A rotatable knob 226 is disposed on the handle and the steering wires are connected to the rotatable knob. Sheaths 227 run up and down the length of the flexible drive shaft housing for the steering wires to slide within. The steering wires are attached to one or more of the steering knuckles.

Rotation of the steering knob on the handle causes the steering wires mounted on opposite sides of the steering knob shaft and pulley 228 to be pulled partially into the handle or to be pushed partially out of the handle depending on the direction of rotation of the steering knob. As the wire is pulled into the handle and through the sheath, the end of the wire which is attached to one of the steering knuckles pulls the knuckle in the direction of the pull and, hence, changes the position of the knuckle and the head or neck of the instrument. This direction and position change allows for steering of the head.

There can be several sets of steering wires. Each set of steering wires can be attached such that they pull on different knuckles. These knuckles can be fabricated so that the pivots which connect one knuckle to the next are oriented so that the direction of rotation is through a different plane than other knuckles in the housing. The fact that steering can occur along different planes means that increased degrees of steering and, thus, increased control over position of the head of the stapler can be achieved.

A substantial advantage to utilizing the knuckles as shown, to steer the instruments of the present invention, is that the knuckles are hollow and allow the incorporation of various mechanisms within the flexible housing without increasing the diameter of the instrument. This is especially important in endoscopic procedures where it is desirable to keep the size of instruments minimal and use as small diameter trocars as possible.

While the invention has been described by way of preferred embodiments, it will be evident that other adaptations and modifications may be employed without departing from the spirit and scope of the present invention.

What is claimed is:

1. An instrument for applying fasteners to tissue during endoscopic surgery, said instrument comprising a handle portion for manipulation outside a body of a mammal, means comprising a business head for applying a fastener to tissue within the body of said mammal; and a housing portion connecting said handle portion to said business head, said housing portion and said business head insertable into said mammal endoscopically through a trocar cannula, said housing portion having a rotatable drive shaft disposed therein and extending from said handle portion to said business head, said drive shaft being torsionally stiff to generate sufficient force to drive a fastener through tissue and apply said fastener to the tissue, and means disposed in said business head for translating the rotational forces of the drive shaft into non-rotational forces for applying said fastener and wherein the means disposed in said business head for translating the rotational forces of the drive shaft into non-rotational forces translates said rotational forces into reciprocating forces for applying said fastener.

2. An instrument according to claim 1 wherein the means disposed in said business head for translating the rotational forces of the drive shaft translates said rotational forces into linear forces for applying said fastener.

3. An instrument according to claim 1 wherein the handle includes means for rotating said rotatable drive shaft.

4. The instrument of claim 1 wherein said business head comprises a linear array of surgical staples.

5. The instrument of claim 1 wherein the business head comprises a circular array of surgical staples.

6. The instrument of claim 1 wherein said business head comprises an array of ligating clips.

7. An instrument for applying fasteners to tissue during endoscopic surgery, said instrument comprising a handle portion for manipulation outside a body of a human, means comprising a business head for applying a fastener to tissue within the body of said human; and a flexible housing portion connecting said handle portion to said business head, said housing portion and said business head insertable into said mammal endoscopically through a trocar cannula, said flexible housing portion having a rotatable, axially flexible, torsionally stiff drive shaft disposed therein and extending from said handle portion to said business head to generate sufficient forces to drive a fastener through tissue and apply said fastener to the tissue and wherein the means disposed in said business head for translating the rotational forces of the drive shaft into non-rotational forces translates said rotational forces into reciprocating forces for applying said fastener.

8. An instrument according to claim 7 which includes means disposed in said flexible housing and extending substantially the entire length of said flexible housing for controlling the position of the flexible housing and business head with respect to said handle portion.

9. The instrument of claim 7 wherein said business head comprises a linear array of surgical staples.

10. The instrument of claim 7 wherein the business head comprises a circular array of surgical staples.

11. The instrument of claim 7 wherein said business head comprises an array of ligating clips.

12. An instrument for applying fasteners to tissue during endoscopic surgery, said instrument comprising a handle portion for manipulation outside the body of a human, means comprising a business head for applying a fastener to tissue within the body of said human; and a flexible housing portion connecting said handle portion to said business head, said housing portion and said business insertable into said mammal endoscopically through a trocar cannula, said flexible housing portion having an axially flexible, torsionally stiff rotatable drive shaft disposed therein and extending from said handle portion to said business head to apply sufficient force to said business head to apply a fastener to tissue, means disposed in said flexible housing for controlling the position of said business head with respect to said handle portion and means disposed in said business head for translating the rotational forces of the drive shaft into non-rotational forces for applying said fastener and wherein the means disposed in said business head for translating the rotational forces of the drive shaft into non-rotational forces translates said rotational forces into reciprocating forces for applying said fastener.

13. An instrument according to claim 12 wherein the means disposed in said business head for translating the rotational forces of the drive shaft translates said rotational forces into linear forces for applying said fastener.

14. An instrument according to claim 12 wherein the handle includes means for rotating said drive shaft.

15. The instrument of claim 12 wherein said business head comprises a linear array of surgical staples.

16. The instrument of claim 12 wherein the business head comprises a circular array of surgical staples.

17. The instrument of claim 12 wherein said business head comprises an array of ligating clips.

* * * * *